US00PP24148P3

(12) United States Plant Patent
Scheffers

(10) Patent No.: US PP24,148 P3
(45) Date of Patent: Jan. 7, 2014

(54) *DRACAENA* PLANT NAMED '2004030D'

(50) Latin Name: *Dracaena fragrans deremensis*
Varietal Denomination: 2004030D

(75) Inventor: Ruud Scheffers, Honselersdijk (NL)

(73) Assignee: Dragon Tree Beheer (NL)

( * ) Notice: Subject to any disclaimer, the term of this patent is extended or adjusted under 35 U.S.C. 154(b) by 79 days.

(21) Appl. No.: 13/385,657

(22) Filed: Feb. 28, 2012

(65) Prior Publication Data

US 2013/0227754 P1 Aug. 29, 2013

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Annette Para
(74) *Attorney, Agent, or Firm* — Cassandra Bright

(57) ABSTRACT

A new and distinct *Dracaena* cultivar named '2004030D' is disclosed, characterized by strong foliage, with a unique dark green edge separated from a grayish green middle by a thin white stripe. The new variety is a *Dracaena*, typically produced as an ornamental plant.

1 Drawing Sheet

Latin name of the genus and species: *Dracaena fragrans deremensis*.

Variety denomination: '2004030D'.

BACKGROUND OF THE INVENTION

The new cultivar is the product of chance discovery. The new variety originated as a naturally occurring mutation of the unpatented 'White Stripe' variety of *Dracaena fragrans deremensis*.

The new variety was discovered by the inventor, Ruud A. M. Scheffers, a citizen of the Netherlands, in July of 2004 in a commercial greenhouse belonging to the inventor in Honselersdijk, The Netherlands. After identifying the new variety as a potentially interesting selection, the inventor continued confidential testing and propagation of '2004030D' for several years, assessing stability of the unique characteristics of this variety. The inventor applied for, and was granted plant breeders rights in the EU, application number 2005/0930, grant number EU20846. A non-certified copy of the application is attached to this specification. During the entire time of the EU application plants were only available in restricted greenhouse areas of the testing site of the CPVO. Commercial availability of the new variety began in early 2012.

Asexual reproduction of the new cultivar '2004030D' was first performed at the commercial greenhouse of the inventor in Honselersdijk, The Netherlands by vegetative cuttings in August of 2004. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar '2004030D' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '2004030D'. These characteristics in combination distinguish '2004030D' as a new and distinct *Dracaena* cultivar:

1. Strong foliage.
2. Leaves are dark green along the edge.
3. Leaves are grayish green in the middle.
4. The leaves' grayish green middle and dark green edge are separated by a thin white stripe.

PARENT COMPARISON

Plants of the new cultivar '2004030D' are similar to the parent, *Dracaena fragrans deremensis* 'White Stripe' unpatented, in most horticultural characteristics. The new variety, however, possesses leaves that are thicker than foliage of 'White Stripe'. Additionally, '2004030D' possesses leaves with a dark green edge compared to the foliage of 'White Stripe', which has a white edge.

COMMERCIAL COMPARISON

'2004030D' is most similar to the parent variety

BRIEF DESCRIPTION OF THE PHOTOGRAPH

The accompanying photograph in FIG. 1 illustrates in full color a typical plant of '2004030D' grown in a commercial greenhouse in Honselersdijk, The Netherlands. This plant is approximately 12 months old, shown planted in a 15 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe '2004030D' plants grown in a greenhouse in Honselersdijk, The Netherlands. Temperature was approximately 20° C. day and night. No artificial light, photoperiodic treatments were given to the plants. The plant was shaded if the sun was shining on it. Measurements and numerical values represent averages of typical plant types.

DETAILED BOTANICAL DESCRIPTION

Botanical classification: *Dracaena fragrans deremensis* '2004030D'.

PROPAGATION

Time to initiate rooting: About 4 weeks at approximately 20° C. 6 weeks to a fully rooted plantlet.

Root description: Moderately thick, moderately fibrous, not fleshy. Young roots near RHS Yellow-White 158 D. Older roots near Greyed-O164D.

PLANT

Age of plant described: Approximately 3 months.
Pot size of plant described: 12 cm pot.
Growth habit: Upright, non branching.
Height: Approximately 29.1 cm.
Plant spread: Approximately 48.7 cm.
Growth rate: Moderate, approximately 8 cm per month.
Branching characteristics: Not free branching, growing with one main stem from the base. Will only develop lateral branches after pinching/pruning.
Diameter of stem: Approximately 1.3 cm.
Internode length: Average 0.8 cm.
Texture of stem: Smooth, dull.
Color of stem: Near RHS Yellow-Green 145C.
Stem strength: Very strong.
Number of leaves per stem: Average 16.

FOLIAGE

Leaf:

*Arrangement*.—Alternate (spirally).
*Average length*.—Approximately 33.3 cm.
*Average width*.—Approximately 5.1 cm.
*Shape of blade*.—Lorate.
*Aspect*.—Slightly curved downward.
*Apex*.—Long acuminate, not sharp.
*Base*.—Broad cuneate.
*Attachment*.—Sheathing.
*Margin*.—Entire.
*Texture of top surface*.—Smooth, glossy.
*Texture of bottom surface*.—Smooth, moderately glossy.
*Color*.—Young foliage upper side: Background both Green RHS N137A and 143A, striped (axial) near White N155D (two conspicuous stripes) and smaller stripes 137C and 138B. Young foliage under side: Background both Green RHS 137C and 138B, striped (axial) near White N155D (two conspicuous stripes), outer margins near in both RHS N137A and 143A. Mature foliage upper side: Background both RHS N137A and Yellow-Green 147A(but darker), striped (axial) near N155D (two conspicuous stripes) and Greyed-Green 191D and 198B. Mature foliage under side: Near RHS Yellow-Green 147B, striped (axial) near N155D (two conspicuous stripes), outer margins near RHS N137A.
*Venation*.—Type: parallel. Color: Upperside: Indistinguishable from leaf blade. Underside: Main vein near RHS 143A, other veins colored as leaf blade.
*Sheath*.—Average Length: Approximately 2.3 cm. Average Width: Approximately 0.8 cm. Color: Central part near RHS Yellow-Green 145C and 145D, margins near RHS Greyed-Green 192D. Texture: Smooth, moderately glossy.

OTHER CHARACTERISTICS

Flower production: Not observed to date.
Disease and pest resistance: Neither resistance nor susceptibility to normal diseases and pests of *Dracaena*.
Drought tolerance and temperature tolerance: Moderately high drought resistance, good heat resistance, to at least 40° C.
Fruit/seed production: Not observed to date.

What is claimed is:

1. A new and distinct cultivar of *Dracaena* plant named '2004030D' as herein illustrated and described.

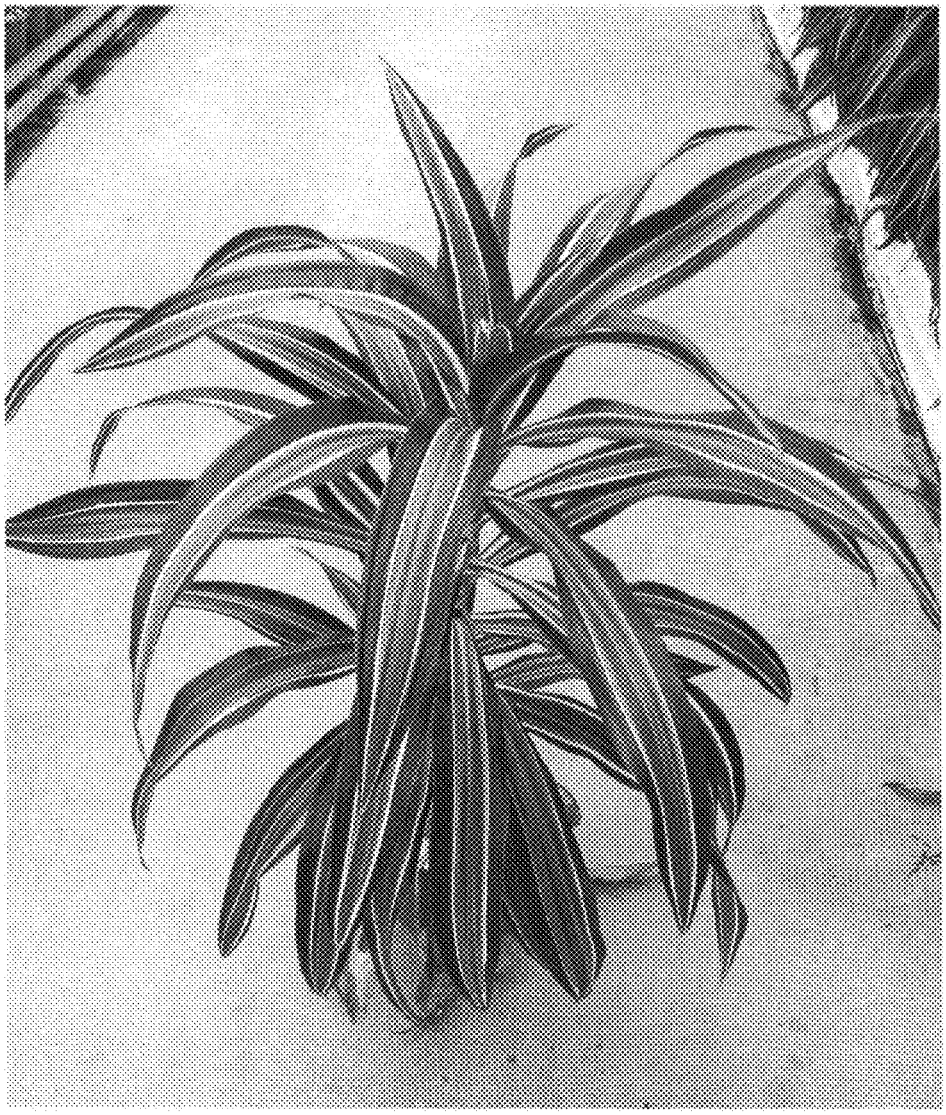

* * * * *